United States Patent
Kim et al.

(10) Patent No.: US 11,280,736 B2
(45) Date of Patent: Mar. 22, 2022

(54) FLUORESCENCE LIFETIME MEASUREMENT DEVICE FOR ANALYZING MULTI-EXPONENTIAL DECAY FUNCTION TYPE EXPERIMENTAL DATA AT HIGH SPEED AND MEASUREMENT METHOD THEREFOR

(71) Applicants: YONSEI UNIVERSITY INDUSTRY FOUNDATION (YONSEI UIF), Seoul (KR); INTEKPLUS CO., LTD., Daejeon (KR)

(72) Inventors: Dug Young Kim, Seoul (KR); Won Sang Hwang, Seoul (KR); Dong Eun Kim, Gwangmyeong-si (KR); Min Gu Kang, Daejeon (KR)

(73) Assignees: YONSEI UNIVERSITY INDUSTRY FOUNDATION (YONSEI UIF), Seoul (KR); INTEKPLUS CO., LTD., Daejeon (KR)

(*) Notice: Subject to any disclaimer, the term of this patent is extended or adjusted under 35 U.S.C. 154(b) by 407 days.

(21) Appl. No.: 16/495,115

(22) PCT Filed: Nov. 17, 2017

(86) PCT No.: PCT/KR2017/013142
§ 371 (c)(1),
(2) Date: Sep. 18, 2019

(87) PCT Pub. No.: WO2018/182125
PCT Pub. Date: Oct. 4, 2018

(65) Prior Publication Data
US 2020/0088638 A1    Mar. 19, 2020

(30) Foreign Application Priority Data
Mar. 31, 2017 (KR) .................. 10-2017-0042007

(51) Int. Cl.
| | | |
|---|---|---|
| G01N 21/64 | (2006.01) | |
| A61B 5/00 | (2006.01) | |
| G06T 5/00 | (2006.01) | |

(52) U.S. Cl.
CPC ........ *G01N 21/6408* (2013.01); *A61B 5/0059* (2013.01); *G01N 21/6458* (2013.01);
(Continued)

(58) Field of Classification Search
CPC ........... G06T 5/008; G06T 2207/10064; G06T 2207/30024; A61B 5/0059
See application file for complete search history.

(56) References Cited

U.S. PATENT DOCUMENTS

| | | |
|---|---|---|
| 9,052,288 B2 | 6/2015 | Hoshishima |
| 9,784,678 B2 | 10/2017 | Ma |

(Continued)

FOREIGN PATENT DOCUMENTS

| | | |
|---|---|---|
| CN | 103090971 A | 5/2013 |
| CN | 105300949 A | 2/2016 |

(Continued)

OTHER PUBLICATIONS

Gafni, Ari et al., "Analysis of Fluorescence Decay Curves by Means of the Laplace Transformation", *Biophysical journal*, vol. 15, Issue 3, Apr. 1975 (pp. 263-280).

(Continued)

*Primary Examiner* — David P Porta
*Assistant Examiner* — Fani Boosalis
(74) *Attorney, Agent, or Firm* — NSIP Law

(57) ABSTRACT

A fluorescence lifetime measuring apparatus according to an embodiment of the present invention includes: an irradiation light generator configured to generate irradiation light; a fluorescence photon detector configured to irradiate at least one or more samples, containing fluorescent molecules, with (Continued)

the irradiation light and collect a fluorescence photon generated by the irradiation; a converter configured to amplify the fluorescence photon and convert the amplified fluorescence photon into a fluorescence signal; and a measurer configured to analyze data of a function of the fluorescence signal by using a function obtained by multiplying a value, which is obtained by integrating the function of the fluorescence signal, by a simulation function.

6 Claims, 2 Drawing Sheets

(52) U.S. Cl.
CPC .... *G06T 5/008* (2013.01); *G06T 2207/10064* (2013.01); *G06T 2207/30024* (2013.01)

(56) References Cited

U.S. PATENT DOCUMENTS

| | | |
|---|---|---|
| 2006/0149479 A1 | 7/2006 | Ma |
| 2009/0216457 A1 | 8/2009 | Ma |
| 2012/0286171 A1 | 11/2012 | Hoshishima |
| 2013/0052656 A1 | 2/2013 | Hoshishima et al. |

FOREIGN PATENT DOCUMENTS

| | | | |
|---|---|---|---|
| JP | 9-229859 A | 9/1997 | |
| JP | 2008-527311 A | 7/2008 | |
| JP | 2011-149891 A | 8/2011 | |
| KR | 10-2011-0121070 A | 11/2011 | |
| KR | 10-2012-0001533 A | 1/2012 | |
| KR | 10-2012-0130772 A | 12/2012 | |
| WO | WO 2006/069444 A1 | 7/2006 | |
| WO | WO 2012/158121 A1 | 11/2012 | |
| WO | WO-2020256972 A1 * | 12/2020 | ......... A61B 1/00009 |

OTHER PUBLICATIONS

Extended European Search Report dated Mar. 2, 2020 in counterpart European Patent Application No. 17903417.8 (9 pages in English).
International Search Report dated Mar. 22, 2018 in counterpart International Patent Application No. PCT/KR2017/013142 (2 pages in English and 2 pages in Korean).
Chinese Office Action dated Jul. 5, 2021 in counterpart Chinese Patent Application No. 201780088945.5 (8 pages in Chinese).
Martin, John L. et al., "A Novel use of Differential Equations to Fit Exponential Functions to Experimental Data," *Journal of neuroscience methods*, vol. 51, Issue 2, Mar. 1994 (pp. 135-146).
Istratov, Andrei A. et al., "Exponential Analysis in Physical Phenomena," *Review of Scientific Instruments*, vol. 70, No. 2, Feb. 1999 (pp. 1233-1257).
Kryzhniy, V. V., "High-Resolution Exponential Analysis via Regularized Numerical Inversion of Laplace Transforms," *Journal of Computational Physics*, vol. 199, Issue 2, Sep. 20, 2004 (pp. 618-630).
European Office Action dated Jun. 30, 2021 in counterpart European Patent Application No. 17903417.8 (9 pages in English).

* cited by examiner

FLUORESCENCE LIFETIME MEASUREMENT DEVICE FOR ANALYZING MULTI-EXPONENTIAL DECAY FUNCTION TYPE EXPERIMENTAL DATA AT HIGH SPEED AND MEASUREMENT METHOD THEREFOR

CROSS REFERENCE TO RELATED APPLICATIONS

This application is a U.S. National Stage Application of International Application No. PCT/KR2017/013142, filed on Nov. 17, 2017, which claims the benefit under 35 USC 119(a) and 365(b) of Korean Patent Application No. 10-2017-0042007, filed on Mar. 31, 2017, in the Korean Intellectual Property Office, the entire disclosure of which is incorporated herein by reference for all purposes.

TECHNICAL FIELD

The following description relates to a fluorescence lifetime measuring apparatus and a fluorescence lifetime measuring method for measuring fluorescence lifetimes, and more particularly to a fluorescence lifetime measuring apparatus and a fluorescence lifetime measuring method, which may independently measure the fluorescence lifetimes for two or more mixed samples with a minimum time.

BACKGROUND ART

Microscopes are divided into a first-generation optical microscope, a second-generation electron microscope, and a third-generation scanning probe microscope, and are used in a wide variety of applications such as medicine, molecular biology, development of new pharmaceuticals, and material engineering.

However, a fluorescence lifetime imaging microscope is now emerging as a key technique in the research of microscopes. The fluorescence lifetime imaging microscope is equipment (FLIM-FRET) which most accurately measures Fluorescence Resonance Energy Transfer (FRET). The FRET is a phenomenon of energy transfer from one fluorescent molecule to another without emission or absorption of light when two fluorescent molecules are positioned at a close distance of 10 nm or less. By using the FRET, phenomena, which occur at a scale of several nm and thus cannot be seen with an optical microscope, may be observed such that the demand is rapidly increasing in many life-science fields such as cell membranes, DNA, RNA, protein-protein interaction, and the like.

Particularly, TCSPC, which is used as the fluorescence lifetime imaging microscope, detects a response of a single photon by using a photodetector, such as PMT or Avalanche Photo Diode (APD), which has a high signal gain. Regardless of whether the shape of a response pulse produced by a single photon has a long width on a time axis, an arrival time of the single photon may be precisely measured. In this manner, a fluorescence lifetime of 0.1 nanoseconds may also be measured. In the case where only the single photon is detected in every measurement, the arrival time of the single photon may be measured by detecting an arrival time of a rising edge of the measured single photon response. The accuracy of the arrival time measurement is in principle irrelevant to an output pulse width of the photodetector. However, the high-gain photodetector has a problem of transit time spread (TTS) in terms of operation principle. Compared to an analog impulse response pulse width in TCSPC, PMT shows about five times higher accuracy in time measurement. The arrival time of the single photon, which is counted in this manner, is used for generating a time-axis histogram by a digital method; and after counting is performed more than hundreds to thousands of times, a fluorescence lifetime may be calculated by performing fitting on an exponential decay function, considering the histogram as a probability distribution function (PDF) of fluorescence photon emission.

As a measurement method with high-sensitivity and stability, TCSPC is widely used in various applications in the field of time-resolved spectroscopy and fluorescence lifetime imaging microscopy (FILM). However, TCSPC basically has a restriction on measurement time in a single photon counting method. In TCSPC, only one photon may be counted at every measurement cycle. Even when multiple fluorescence photons are generated from multiple fluorescent molecules by an excitation light pulse, it is required to intentionally reduce the intensity of photons counted by a counter, so that only one photon should be generated per pulse. If two or more photons are detected by the counter within a measurement cycle, particularly if arrival times of two photons are too close to be split into two pulses, the counter counts only a value of a photon arriving first, such that signal loss occurs, resulting in a shorter fluorescence lifetime than an actual value.

Further, even in a single photon, if a plurality of samples having two or more different fluorescence lifetimes are mixed, there may be many more problems in measuring fluorescence lifetimes independently.

That is, with respect to data having a mixture of two or more exponential decay functions, by calculating a decay constant of each exponential decay function and a proportion of a specific exponential decay function in the total data, components of an object to be measured may be analyzed. Such calculation may be generally performed by non-linear least-square curve fitting, in which a mathematical model of the exponential decay function is set up, and is compared with experimental data by adjusting parameters of the mathematical model, to obtain a parameter having the greatest difference therebetween. However, the non-linear least square curve fitting method uses a repetitive algorithm which compares a model function with the measured data by repeatedly adjusting parameters until a difference between the model function and the measured data becomes a minimum. If a difference between the model function and the measured data is less than a given tolerance condition, the non-linear least square curve fitting method terminates calculation, such that there is a disadvantage in that the method may obtain only approximate values of parameters. Further, the algorithm is an algorithm which repeats calculations until the tolerance condition is satisfied, thus leading to a great number of computations for obtaining a desired value. In the case of MRI or FILM equipment for image configuration, it is required to analyze multiple fluorescence signals of hundreds of thousands to millions of pixels constituting a two-dimensional or three-dimensional image, such that there is a drawback in that a computation time for completing the entire image is very long.

DISCLOSURE

Technical Problem

According to an embodiment of the present invention, a fluorescence lifetime measuring apparatus and a fluorescence lifetime measuring method are provided, which may measure fluorescence lifetimes independently at a fast speed even when two or more fluorescence samples having different fluorescence lifetimes are mixed.

Technical Solution

In accordance with one aspect of the present invention, there is provided a fluorescence lifetime measuring apparatus, including: an irradiation light generator configured to generate irradiation light; a fluorescence photon detector configured to irradiate at least one or more samples, containing fluorescent molecules, with the irradiation light and collect a fluorescence photon generated by the irradiation; a converter configured to amplify the fluorescence photon and convert the amplified fluorescence photon into a fluorescence signal; and a measurer configured to analyze data of a function of the fluorescence signal by using a function obtained by multiplying a value, which is obtained by integrating the function of the fluorescence signal, by a simulation function.

In accordance with another aspect of the present invention, there is provided a fluorescence lifetime measuring method, including: generating irradiation light; irradiating at least one or more samples with the irradiation light and collecting a fluorescence photon generated by the irradiation; converting the fluorescence photon into a fluorescence signal; and measuring by analyzing data of a function of the fluorescence signal by using a function obtained by multiplying a value, which is obtained by integrating the function of the fluorescence signal, by a simulation function.

Advantageous Effect

According to an embodiment of the present invention, even when two or more samples having different fluorescence lifetimes are mixed, fluorescence lifetime values of the samples may be calculated more rapidly.

BEST MODE FOR CARRYING OUT THE INVENTION

Advantages and features of the present invention and methods of accomplishing the same may be understood more readily by reference to the following detailed description of exemplary embodiments and accompanying drawings. The present invention may, however, be embodied in many different forms and should not be construed as being limited to the embodiments set forth herein. Rather, these embodiments are provided so that this disclosure will be thorough and complete and will fully convey the concept of the invention to those skilled in the art, and the present invention will only be defined by the appended claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinafter, a fluorescence lifetime measuring apparatus 100 according to an embodiment of the present invention will be described with reference to the accompanying drawings.

Figure 1:
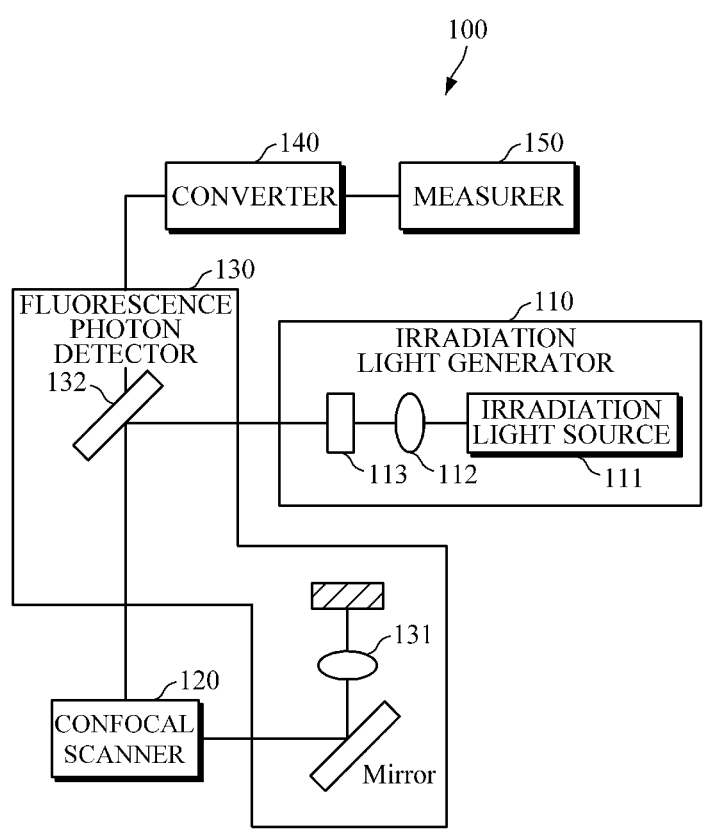
FIG. 1 is a block diagram illustrating a fluorescence lifetime measuring apparatus according to an embodiment of the present invention.

FIG. 1 is a block diagram illustrating the fluorescence lifetime measuring apparatus 100 according to an embodiment of the present invention. Referring to FIG. 1, an irradiation light generator 110 may generate irradiation light to excite a sample S. The irradiation light is incident in parallel on a collimator 112 in the form of a pulse with respect to time.

The incident irradiation light passes through a Short Pass Filter (SPF) 113 and is reflected from a dichroic filter 320, to be incident into the sample S through an objective lens 131. The incident irradiation light allows for generation of fluorescence photons from the sample S.

The generated fluorescence photons are collected into a confocal scanner 120 through the objective lens 131, to pass through the dichroic filter 132.

Then, the fluorescence photons are amplified by the converter 140 to be transformed into a fluorescence signal, and the amplified fluorescence signal is transmitted to the measurer 150. The measurer 150 calculates a fluorescence lifetime of the fluorescence photons based on the received fluorescence signal.

The irradiation light generator 110 includes an irradiation light source 111 as a structure for generating irradiation light to be irradiated to the sample S containing fluorescent molecules.

The irradiation light has a pulse width of 100 psec or less and a wavelength of 300 nm to 700 nm. The irradiation light source 111 according to an embodiment of the present invention includes a semiconductor laser.

Further, the semiconductor laser may include an electric pulse signal generator having a pulse width of 300 ps or less, a pulse clock generator for generating a stable trigger signal, and a semiconductor pulse laser head having a wavelength of 400 nm.

The irradiation light generator 110 may further include the collimator 112 and the SPF 113 for collecting the irradiation light.

The confocal scanner 120 allows for three-dimensional imaging, such that a change in the sample S with time of light or with wavelength may be measured three-dimensionally.

The confocal scanner 120 according to an embodiment of the present invention includes a horizontal scanner and a vertical scanner. The horizontal scanner includes a galvanometer mirror, and may scan two-dimensionally at ultra-high speed using the galvanometer mirror. The vertical scanner includes a motor-driven means or a piezoelectric-driven means (PZT). Both the motor-driven means and the piezoelectric-driven means may be controlled by means of an open loop system or a closed loop system.

A fluorescence photon detector 130 is a module for irradiating one or more samples S with the irradiation light and collecting multiple fluorescence photons which are generated by the irradiation. The fluorescence photon detector 130 includes a fluorescence photon collecting lens 131, and a dichroic filter 132 for preventing the irradiation light from being received by the converter 140 which will be described later.

The fluorescence photon collecting lens 131 is a lens for collecting multiple fluorescence photons generated from the samples S. The fluorescence photon collecting lens 131 may serve as an objective lens.

The dichroic filter 132 is an optical filter which selectively passes the incident irradiation light according to wavelengths. The dichroic filter 132 according to an embodiment of the present invention has characteristics of reflecting a wavelength band corresponding to the irradiation light and passing a wavelength band corresponding to the fluorescence photons. However, the wavelength band to be reflected or passed by the dichroic filter 132 may be adjusted as needed.

Further, the fluorescence photons, from which the irradiation light is removed, pass through a loss-pass filter (LPF), to be collected by a collimator (not shown) of the fluorescence photon detector.

The converter 140 is a module for amplifying the fluorescence photons, having passed through the dichroic filter 132, and converting the amplified fluorescence photons into a fluorescence signal. The converter 140 includes a photodetector, an amplifier, and a digitizer.

The photodetector and the amplifier according to an embodiment of the present invention includes a Photo Multiply Tube (PMT), an Avalanche Photo Diode (APD) and/or LPF, and an AMP.

The photodetector converts the collected fluorescence photons into a fluorescence signal. The fluorescence signal obtained by the conversion is transmitted to the LPF.

The LPF is a filter for passing a low-frequency signal, and may temporally amplify a clock signal. The LPF according to an embodiment of the present invention includes an electronic Gaussian Low-Pass Filter (GLPF).

The GLPF removes a high-frequency component to facilitate data processing of the converted clock signal. The GLPF is symmetric without the occurrence of ringing. The GLPF reduces a bandwidth of the clock signal so as to correspond to a bandwidth of the digitizer.

The digitizer recovers the signal by considering the irradiation light having a small pulse width. Specifically, the digitizer collects clock signals, and functions as part of an AMD measurer 150 which calculates a fluorescence lifetime based on the collected clock signals.

The measurer 150 is a module for calculating the fluorescence lifetime of the fluorescence photons collected from at least one or more samples. The measurer 150 may measure the fluorescence lifetime based on the following principle.

The measurer 150 may measure the fluorescence lifetime for at least one or more samples, in which the measurements for the one or more samples may be performed by the following method.

The most intuitive method to measure the fluorescence lifetime includes measuring a time waveform of fluorescence, which is emitted after excitation light having a short pulse width is incident on a sample, by using a high-speed photodetector. A pulse-type laser is used as the excitation light having a short pulse width.

In this case, by defining data of each sample as $I(t)$, $I(t)$ may be described by a sum of exponential decay functions with n number, which may be represented by the following Equation.

$$I(t) = \sum_{i=1}^{n} c_i e^{-t/\tau_i} = c_1 e^{-t/\tau_1} + c_2 e^{-t/\tau_2} + c_3 e^{-t/\tau_3} + \ldots \quad \text{[Equation 1]}$$

Herein, $\tau_i$ is an i-th exponential decay constant, and $c_i$ is a constant representing a mixture proportion of the i-th exponential decay function in the total functions. By defining, as $f(t)$, a function obtained by normalizing $I(t)$ so that an integral value of $I(t)$ becomes 1, $f(t)$ may be represented by the following Equation.

$$f(t) \equiv \frac{I(t)}{\int_{-\infty}^{\infty} I(t) dt} = \quad \text{[Equation 2]}$$
$$\frac{1}{A} \sum_{i=1}^{n} c_i e^{-t/\tau_i} = \frac{1}{A}[c_1 e^{-t/\tau_1} + c_2 e^{-t/\tau_2} + c_3 e^{-t/\tau_3} + \ldots]$$

Herein, A has the following Equation.

$$A = \sum_{i}^{n} c_i \int_{0}^{\infty} e^{-t/\tau_i} dt = \sum_{i}^{n} c_i \tau_i \quad \text{[Equation 3]}$$

Herein, $I(t)$ is measured data, and $f(t)$ is a function obtained by normalizing $I(t)$ so that an integral value of $I(t)$ becomes 1. That is, by integrating the function $f(t)$, $\int_{-\infty}^{\infty} f(t)dt=1$. That is, $f(t)$ has an integral value of 1 with respect to a time axis, such that $f(t)$ may be a type of probability distribution function for the time variable. In the case where the measured data in Equation 1 is composed of a mixture of n number of exponential decay functions, 2n number of simultaneous equations are required in order to obtain n number of exponential decay constants $\tau_1, \tau_2, \ldots, \tau_n$, and n number of constants $c_1, c_2, \ldots, c_n$ which represent mixture proportions of the exponential decay functions. In this case, under the condition that the sum of the mixture proportions of the functions must equal 1, the following Equation may be obtained.

$$\sum_{i}^{n} c_i = 1 \quad \text{[Equation 4]}$$

In addition to the above Equations, an equation is needed which may represent 2n-1 number of simultaneous equations related to the exponential decay constants $\tau_1, \tau_2, \ldots, \tau_n$, and the n number of constants $c_1, c_2, \ldots, c_n$ which represent mixture proportions of the exponential decay functions.

Here, a simulation function may be an equation in the form of an exponential function. That is, the simulation function $g(t)$ may be represented by, for example, $g_k(t) \equiv e^{t/a_k}$.

In this case, a value obtained by integrating a function $g_k(t) \equiv e^{t/a_k}$, which is obtained by multiplying the function $I(t)$ of the fluorescence signal by the simulation function, may be represented by the following Equation, whereby a fluorescence lifetime of each sample may be calculated.

$$\langle f \cdot g_k \rangle = \int_{-\infty}^{\infty} e^{-t/a_k} f(t) dt = \quad \text{[Equation 5]}$$
$$\frac{1}{A} \sum_{i}^{n} c_i \int_{0}^{\infty} e^{-t(1/\tau_i + 1/a_k)} dt = \frac{1}{A} \sum_{i}^{n} c_i \left( \frac{\tau_i a_k}{\tau_i + a_k} \right) \equiv D_k$$

By using the above Equation 5, simultaneous equations related to c and $\tau$ may be formed. That is, in the case where the measured data is composed of a sum of exponential decay functions with n number, 2n−1 number of simultaneous equations may be obtained by using Equation 5, and by using Equation 4 together, 2n number of simultaneous equations related to the n number of exponential decay constants $\tau_1, \tau_2, \ldots, \tau_n$, and the n number of constants $c_1, c_2, \ldots, c_n$ which represent mixture proportions of the exponential decay functions may be obtained. By obtaining solutions to the 2n number of simultaneous equations, a modelling function of experimental data may be calculated very accurately and rapidly without a large number of repetitive calculations.

Further, in another example, the simulation function may be an equation in the form of a radical root function. That is, the simulation function g(t) may be represented by, for example, $g_k(t) \equiv \sqrt[k]{t}$.

In this case, a value obtained by integrating a function $g_k(t) \equiv \sqrt[k]{t}$, which is obtained by multiplying the function I(t) of the fluorescence signal by the simulation function, may be represented by the following Equation, whereby a fluorescence lifetime of each sample may be calculated.

$$\langle f \cdot g_k \rangle = \int_0^\infty \sqrt[k]{t}\, f(t)dt = \frac{1}{A} \sum_i^n c_i \int_0^\infty \sqrt[k]{t}\, e^{-t/\tau_i} dt = \quad \text{[Equation 6]}$$

$$\frac{1}{A} \sum_i^n c_i \tau_i^{(1+1/k)} \Gamma(1+1/k) \equiv F_k$$

By using the above Equation 6, simultaneous equations related to c and τ may be formed. That is, in the case where the measured data is composed of a sum of exponential decay functions with n number, 2n−1 number of simultaneous equations may be obtained by using Equation 6, and by using Equation 4 together, 2n number of simultaneous equations related to the n number of exponential decay constants $\tau_1, \tau_2, \ldots, \tau_n$, and the n number of constants $c_1, c_2, \ldots, c_n$ which represent mixture proportions of the exponential decay functions may be obtained. By obtaining solutions to the 2n number of simultaneous equations, a modelling function of experimental data may be calculated very accurately and rapidly without a large number of repetitive calculations.

In addition, in yet another example, the simulation function may be an equation in the form of a sine function. That is, the simulation function g(t) may be represented by, for example, $g_k(t) \equiv \sin(t/a_k)$.

In this case, a value obtained by integrating a function $g_k(t) \equiv \sin(t/a_k)$, which is obtained by multiplying the function I(t) of the fluorescence signal by the simulation function, may be represented by the following Equation, whereby a fluorescence lifetime of each sample may be calculated.

$$\langle f \cdot g_k \rangle = \int_0^\infty \sin(t/a_k) f(t)dt = \quad \text{[Equation 7]}$$

$$\frac{1}{A} \sum_i^n c_i \int_0^\infty \sin(t/a_k) e^{-t/\tau_i} dt = \frac{1}{A} \sum_i^n c_i \frac{a_k \tau_i^2}{a_k^2 + \tau_i^2} \equiv G_k$$

By using the above Equation 7, simultaneous equations related to c and τ may be formed. That is, in the case where the measured data is composed of a sum of exponential decay functions with n number, 2n−1 number of simultaneous equations may be obtained by using Equation 7, and by using Equation 4 together, 2n number of simultaneous equations related to the n number of exponential decay constants $\tau_1, \tau_2, \ldots, \tau_n$, and the n number of constants $c_1, c_2, \ldots, c_n$ which represent mixture proportions of the exponential decay functions may be obtained. By obtaining solutions to the 2n number of simultaneous equations, a modelling function of experimental data may be calculated very accurately and rapidly without a large number of repetitive calculations.

Moreover, in still another example, the simulation function may be an equation in the form of a cosine function. That is, the simulation function g(t) may be represented by, for example, $g_k(t) \equiv \cos(t/a_k)$.

In this case, a value obtained by integrating a function $g_k(t) \equiv \cos(t/a_k)$, which is obtained by multiplying the function I(t) of the fluorescence signal by the simulation function, may be represented by the following Equation, whereby a fluorescence lifetime of each sample may be calculated.

$$\langle f \cdot g_k \rangle = \int_0^\infty \cos(t/a_k) f(t)dt = \quad \text{[Equation 8]}$$

$$\frac{1}{A} \sum_i^n c_i \int_0^\infty \cos(t/a_k) e^{-t/\tau_i} dt = \frac{1}{A} \sum_i^n c_i \frac{a_k^2 \tau_i}{a_k^2 + \tau_i^2} \equiv H_k$$

By using the above Equation 8, simultaneous equations related to c and τ may be formed. That is, in the case where the measured data is composed of a sum of exponential decay functions with n number, 2n−1 number of simultaneous equations may be obtained by using Equation 8, and by using Equation 4 together, 2n number of simultaneous equations related to the n number of exponential decay constants $\tau_1, \tau_2, \ldots, \tau_n$, and the n number of constants $c_1, c_2, \ldots, c_n$ which represent mixture proportions of the exponential decay functions may be obtained. By obtaining solutions to the 2n number of simultaneous equations, a modelling function of experimental data may be calculated very accurately and rapidly without a large number of repetitive calculations.

Furthermore, in still another example, the simulation function may be an equation in the form of a hyper-sine function. That is, the simulation function g(t) may be represented by, for example, $g_k(t) \equiv \sinh(t/a_k)$.

In this case, a value obtained by integrating a function $g_k(t) \equiv \sinh(t/a_k)$, which is obtained by multiplying the function I(t) of the fluorescence signal by the simulation function, may be represented by the following Equation, whereby a fluorescence lifetime of each sample may be calculated.

$$\langle f \cdot g_k \rangle = \quad \text{[Equation 9]}$$

$$\frac{1}{A} \sum_i^n c_i \int_0^\infty \sinh(t/a_k) e^{-t/\tau_i} dt = \frac{1}{A} \sum_i^n c_i \frac{a_k \tau_i^2}{a_k^2 - \tau_i^2} \equiv L_k$$

By using the above Equation 9, simultaneous equations related to c and τ may be formed. That is, in the case where the measured data is composed of a sum of exponential decay functions with n number, 2n−1 number of simultaneous equations may be obtained by using Equation 9, and by using Equation 4 together, 2n number of simultaneous equations related to the n number of exponential decay constants $\tau_1, \tau_2, \ldots, \tau_n$, and the n number of constants $c_1, c_2, \ldots, c_n$ which represent mixture proportions of the exponential decay functions may be obtained. By obtaining solutions to the 2n number of simultaneous equations, a modelling function of experimental data may be calculated very accurately and rapidly without a large number of repetitive calculations.

Moreover, in still another example, the simulation function may be an equation in the form of a hyper-cosine function. That is, the simulation function g(t) may be represented by, for example, $g_k(t) \equiv \cos h(t/a_k)$.

In this case, a value obtained by integrating a function $g_k(t) \equiv \cos h(t/a_k)$, which is obtained by multiplying the function I(t) of the fluorescence signal by the simulation function, may be represented by the following Equation, whereby a fluorescence lifetime of each sample may be calculated.

$$\langle f \cdot g_k \rangle = \frac{1}{A}\sum_i^n c_i \int_0^\infty \cosh(t/a_k) e^{-t/\tau_i} dt = \frac{1}{A}\sum_i^n c_i \frac{a_k^2 \tau_i}{a_k^2 - \tau_i^2} \equiv M_k \quad \text{[Equation 10]}$$

By using the above Equation 10, simultaneous equations related to c and τ may be formed. That is, in the case where the measured data is composed of a sum of exponential decay functions with n number, 2n−1 number of simultaneous equations may be obtained by using Equation 10, and by using Equation 4 together, 2n number of simultaneous equations related to the n number of exponential decay constants $\tau_1, \tau_2, \ldots, \tau_n$, and the n number of constants $c_1, c_2, \ldots, c_n$ which represent mixture proportions of the exponential decay functions may be obtained. By obtaining solutions to the 2n number of simultaneous equations, a modelling function of experimental data may be calculated very accurately and rapidly without a large number of repetitive calculations.

In addition, in yet another example, the simulation function may be an equation in the form of a Bessel function. That is, the simulation function g(t) may be represented by, for example, $g_{mk}(t) \equiv J_m(t/a_k)$.

In this case, a value obtained by integrating a function $g_{mk}(t) \equiv J_m(t/a_k)$, which is obtained by multiplying the function I(t) of the fluorescence signal by the simulation function, may be represented by the following Equation, whereby a fluorescence lifetime of each sample may be calculated.

$$\langle f \cdot g_{mk} \rangle = \frac{1}{A}\sum_i^n c_i \int_0^\infty J_m(t/a_k) e^{-t/\tau_i} dt = \frac{1}{A}\sum_i^n c_i \frac{a_k \tau_i}{\sqrt{a_k^2 + \tau_i^2}} \left[\sqrt{1 + \frac{a_k^2}{\tau_i^2}} + \frac{a_k}{\tau_i}\right]^m \equiv P_{mk} \quad \text{[Equation 11]}$$

By using the above Equation 11, simultaneous equations related to c and τ may be formed. That is, in the case where the measured experimental data is composed of a sum of exponential decay functions with n number, 2n−1 number of simultaneous equations may be obtained by using Equation 11, and by using Equation 4 together, 2n number of simultaneous equations related to the n number of exponential decay constants $\tau_1, \tau_2, \ldots, \tau_n$, and the n number of constants $c_1, c_2, \ldots, c_n$ which represent mixture proportions of the exponential decay functions may be obtained. By obtaining solutions to the 2n number of simultaneous equations, a modelling function of experimental data may be calculated very accurately and rapidly without a large number of repetitive calculations.

The existing average delay method may obtain only an average value of two fluorescence lifetimes by using a calculation formula, such that the method may not obtain fluorescence lifetime values independently by separating mixed samples based on fluorescence lifetimes. By contrast, the above method of the present invention may independently calculate fluorescence lifetimes of the mixed samples.

Furthermore, by using the above method of the present invention, fluorescence lifetime values for more than three fluorescence samples may be obtained individually.

In addition, among devices using fluorescence lifetime imaging microscopy (FLIM), the fluorescence lifetime measuring apparatus 100 may be used for a measurement device using a Time-Correlated Single Photon Counting (TC-SPC) method. However, the fluorescence lifetime measuring apparatus 100 is not limited thereto, and may also be used for a measurement device using an Analog Mean Delay (AMD) method.

The configuration of the fluorescence lifetime measuring apparatus 100 according to an embodiment of the present invention is described above. A fluorescence lifetime measuring method 200 according to an embodiment of the present invention will be described below. The fluorescence lifetime measuring method 200 includes processes performed by the fluorescence lifetime measuring apparatus 100 illustrated in FIG. 1. Accordingly, descriptions overlapping those given above will be omitted, and descriptions of the omitted portions also apply to the fluorescence lifetime measuring method 200 according to an embodiment of the present invention.

Figure 2:
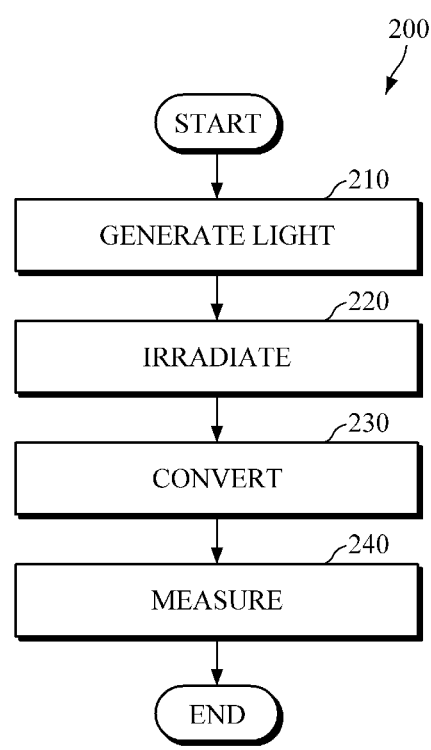
FIG. 2 is a flowchart illustrating a fluorescence lifetime measuring method according to an embodiment of the present invention.

FIG. 2 is a flowchart illustrating a fluorescence lifetime measuring method 200 according to an embodiment of the present invention.

Generating of light in 210 includes: providing at least one or more samples S having different fluorescence lifetimes for the fluorescence lifetime measuring apparatus 100; and generating irradiation light to be irradiated to the samples S.

Irradiating in 220 includes irradiating the samples S with the irradiation light. In this case, the fluorescence photon collector detects fluorescence photons generated from the samples S.

Converting in 230 includes amplifying the collected fluorescence photons and converting the amplified fluorescence photons into a fluorescence signal.

Measuring in 240 includes analyzing data of a function of the fluorescence signal by using a function obtained by multiplying a value, which is obtained by integrating the function of the fluorescence signal, by a simulation function. The function of the fluorescence signal, the value obtained by integrating the function of the fluorescence signal, and the simulation function are based on the above principle.

The invention claimed is:

1. A fluorescence lifetime measuring apparatus, comprising:
   an irradiation light generator configured to generate irradiation light;
   a fluorescence photon detector configured to irradiate at least one or more samples, containing fluorescent molecules, with the irradiation light and collect a fluorescence photon generated by the irradiation;

a converter configured to amplify the fluorescence photon and convert the amplified fluorescence photon into a fluorescence signal; and a measurer configured to analyze data of a function of the fluorescence signal by using a function obtained by multiplying a value, which is obtained by integrating the function of the fluorescence signal, by a simulation function, wherein by defining the function of the fluorescence signal as I(t), the I(t) is calculated using the following equation $$I(t) = \sum_{i=1}^{n} c_i e^{-t/\tau_i} = c_1 e^{-t/\tau_1} + c_2 e^{-t/\tau_2} + c_3 e^{-t/\tau_3} + \ldots \ .$$

2. The apparatus of claim 1, wherein by defining, as $f(t)$, the value obtained by integrating the I(t), the $f(t)$ is normalized to 1, to be calculated using the following equation $$f(t) \equiv \frac{I(t)}{\int_{-\infty}^{\infty} I(t)dt} =$$

$$\frac{1}{A}\sum_{i=1}^{n} c_i e^{-t/\tau_i} = \frac{1}{A}[c_1 e^{-t/\tau_1} + c_2 e^{-t/\tau_2} + c_3 e^{-t/\tau_3} + \ldots \ ],$$

wherein $$A = \sum_{i}^{n} c_i \int_{0}^{\infty} e^{-t/\tau_i} dt = \sum_{i}^{n} c_i \tau_i.$$

3. The apparatus of claim 2, wherein by defining the simulation function as g(t), the g(t) is an exponential function, and a value obtained by multiplying a value, which is obtained by integrating the I(t), by the simulation function g(t) is represented by the following equation $$<f \cdot g_k> = \int_{-\infty}^{\infty} e^{-t/a_k} f(t)dt =$$

$$\frac{1}{A}\sum_{i}^{n} c_i \int_{0}^{\infty} e^{-t(1/\tau_i + 1/a_k)} dt = \frac{1}{A}\sum_{i}^{n} c_i \left(\frac{\tau_i a_k}{\tau_i + a_k}\right) \equiv D_k.$$

4. A fluorescence lifetime measuring method, comprising:
generating irradiation light;
irradiating at least one or more samples with the irradiation light and collecting a fluorescence photon generated by the irradiation;
converting the fluorescence photon into a fluorescence signal; and
measuring by analyzing data of a function I(t) of the fluorescence signal by using a function obtained by multiplying a value, which is obtained by integrating the function I(t) of the fluorescence signal, by a simulation function,
wherein the function I(t) of the fluorescence signal is calculated using the following equation $$I(t) = \sum_{i=1}^{n} c_i e^{-t/\tau_i} = c_1 e^{-t/\tau_1} + c_2 e^{-t/\tau_2} + c_3 e^{-t/\tau_3} + \ldots \ .$$

5. The method of claim 4, wherein by defining the value, obtained by integrating the I(t) as $f(t)$, the $f(t)$ is normalized to 1, to be calculated using the following equation $$f(t) \equiv \frac{I(t)}{\int_{-\infty}^{\infty} I(t)dt} =$$

$$\frac{1}{A}\sum_{i=1}^{n} c_i e^{-t/\tau_i} = \frac{1}{A}[c_1 e^{-t/\tau_1} + c_2 e^{-t/\tau_2} + c_3 e^{-t/\tau_3} + \ldots \ ],$$

wherein $$A = \sum_{i}^{n} c_i \int_{0}^{\infty} e^{-t/\tau_i} dt = \sum_{i}^{n} c_i \tau_i.$$

6. The method of claim 5, wherein by defining the simulation function as g(t), the g(t) is an exponential function, and a value obtained by multiplying a value, which is obtained by integrating the I(t), by the simulation function g(t) is represented by the following equation $$\langle f \cdot g_k \rangle =$$

$$\int_{-\infty}^{\infty} e^{-t/a_k} f(t)dt = \frac{1}{A}\sum_{i}^{n} c_i \int_{0}^{\infty} e^{-t(1/\tau_i + 1/a_k)} dt = \frac{1}{A}\sum_{i}^{n} c_i \left(\frac{\tau_i a_k}{\tau_i + a_k}\right) \equiv D_k.$$

\* \* \* \* \*